(12) United States Patent
Rapier et al.

(10) Patent No.: US 11,083,295 B2
(45) Date of Patent: Aug. 10, 2021

(54) TUBE RACK APPARATUS

(71) Applicant: DEPUY SYNTHES PRODUCTS, INC., Raynham, MA (US)

(72) Inventors: Rhett A. Rapier, Trimbach (CH); Peter Schmid, Zuchwil (CH); Roland Huber, Hagglingen (CH); John Anastasiadis, Tinton Falls, NJ (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 16/372,973

(22) Filed: Apr. 2, 2019

(65) Prior Publication Data

US 2020/0315349 A1 Oct. 8, 2020

(51) Int. Cl.
*A47B 88/988* (2017.01)
*A47B 88/994* (2017.01)
(Continued)

(52) U.S. Cl.
CPC ........ *A47B 88/988* (2017.01); *A47B 87/0207* (2013.01); *A47B 88/994* (2017.01); *B01L 9/06* (2013.01); *G09F 3/0295* (2013.01); *A47B 81/007* (2013.01); *A47F 7/28* (2013.01); *A47F 7/283* (2013.01); *A47G 23/0608* (2013.01); *A47G 23/0641* (2013.01)

(58) Field of Classification Search
CPC .......... B01L 9/06; B01L 9/065; A47B 88/988; A47B 87/0207; A47B 88/994; A47B 81/007; G09F 3/0295; G09F 3/08; A47F 5/00; A47F 7/28; A47F 7/283; A47G 23/0608; A47G 23/0641

USPC ............ 211/85.18, 85.13; 206/446, 443, 370
See application file for complete search history.

(56) References Cited

U.S. PATENT DOCUMENTS 118,451 A * 8/1871 Harris ...................... A47K 1/09
211/65
742,581 A * 10/1903 Burtch ..................... A47K 1/09
211/65
(Continued)

FOREIGN PATENT DOCUMENTS

DE         91 01 408.5 U1    6/1992
IN         286865-0001 A     9/2016
WO         2009024189 A2     2/2009

OTHER PUBLICATIONS

International Search Report dated Jun. 8, 2020 in connection with PCT PCT /IB2020/053054.
(Continued)

*Primary Examiner* — Jonathan Liu
*Assistant Examiner* — Devin K Barnett
(74) *Attorney, Agent, or Firm* — Kramer Amado

(57) ABSTRACT

A tube rack apparatus including a bottom portion having a first length, a plurality of indents formed in the bottom portion and configured to receive tubes and keep tubes straight, the plurality of indents exposing a lower surface of the bottom portion, wherein inserted tubes do not pass through the lower surface of the bottom portion, a plurality of legs extending from the bottom portion, a top portion having a second length longer than the first length, a plurality of openings formed in the top portion, the plurality of openings aligned with the plurality of indents, and at least one handle member extending from a first end of the top portion.

7 Claims, 19 Drawing Sheets

(51) Int. Cl.
*A47B 87/02* (2006.01)
*B01L 9/06* (2006.01)
*G09F 3/00* (2006.01)
*A47B 81/00* (2006.01)
*A47F 7/28* (2006.01)
*A47G 23/06* (2006.01)

(56) References Cited

U.S. PATENT DOCUMENTS

| | | | | |
|---|---|---|---|---|
| 857,763 A * | 6/1907 | Smith | | B25H 3/003 |
| | | | | 211/69 |
| 1,092,156 A * | 4/1914 | Mathis | | A61L 2/00 |
| | | | | 206/207 |
| 1,733,868 A * | 10/1929 | Durell | | A47F 7/0028 |
| | | | | 211/70.6 |
| 2,046,864 A * | 7/1936 | Baker | | B01 9/00 |
| | | | | 422/560 |
| D169,077 S * | 3/1953 | Mains | | D6/682.2 |
| 2,637,299 A * | 5/1953 | Salkey | | A45C 11/34 |
| | | | | 206/214 |
| 2,815,863 A * | 12/1957 | Larson | | A47B 81/007 |
| | | | | 211/70.1 |
| D185,807 S * | 8/1959 | Antle | | D22/107 |
| 2,979,210 A | 4/1961 | Patterson | | |
| 3,298,531 A * | 1/1967 | Wilcke | | B25H 3/04 |
| | | | | 211/70.6 |
| 3,480,152 A * | 11/1969 | Walsh | | B01L 9/06 |
| | | | | 211/74 |
| 3,643,812 A * | 2/1972 | Mander | | B01L 9/06 |
| | | | | 211/74 |
| 3,759,538 A * | 9/1973 | Fabiano | | B62B 3/102 |
| | | | | 280/47.35 |
| 3,762,594 A * | 10/1973 | Utz | | B65D 1/243 |
| | | | | 220/516 |
| 3,940,249 A * | 2/1976 | McClurg | | B01L 7/02 |
| | | | | 436/174 |
| D240,239 S * | 6/1976 | Calandrino | | D24/230 |
| D245,118 S | 7/1977 | Heaton | | |
| 4,111,754 A * | 9/1978 | Park | | B01L 3/5025 |
| | | | | 422/504 |
| D250,348 S * | 11/1978 | Frangiosa | | D24/230 |
| 4,124,122 A * | 11/1978 | Emmitt | | B01L 9/06 |
| | | | | 211/74 |
| 4,160,803 A * | 7/1979 | Potts | | B01L 1/52 |
| | | | | 422/527 |
| D257,390 S | 10/1980 | Hahn | | |
| D258,145 S * | 2/1981 | Potts | | D24/230 |
| 4,284,603 A * | 8/1981 | Korom | | B01L 9/06 |
| | | | | 210/323.1 |
| D265,126 S | 6/1982 | Beall | | |
| 4,407,958 A * | 10/1983 | DeGraff, Jr. | | B01L 9/06 |
| | | | | 211/194 |
| 4,438,068 A * | 3/1984 | Forrest | | B01L 9/06 |
| | | | | 422/430 |
| 4,495,150 A * | 1/1985 | Cook | | B01L 9/06 |
| | | | | 422/527 |
| D283,946 S * | 5/1986 | Chase | | D3/315 |
| D284,700 S * | 7/1986 | Mehra | | D24/229 |
| D288,484 S | 2/1987 | Mitchell | | |
| 4,773,544 A * | 9/1988 | McCarthy | | B43K 23/002 |
| | | | | 206/214 |
| 4,972,947 A * | 11/1990 | McCarthy | | B43M 99/006 |
| | | | | 206/214 |
| 5,011,028 A * | 4/1991 | Sweeney | | A47F 7/0028 |
| | | | | 211/207 |
| D318,332 S | 7/1991 | Allen | | |
| 5,047,210 A * | 9/1991 | Melet | | B01L 9/06 |
| | | | | 211/70 |
| 5,080,232 A * | 1/1992 | Leoncavallo | | B01L 9/06 |
| | | | | 206/443 |
| 5,128,105 A * | 7/1992 | Berthold | | B01L 9/06 |
| | | | | 422/561 |
| 5,133,939 A * | 7/1992 | Mahe | | B01L 9/06 |
| | | | | 211/74 |
| 5,244,700 A * | 9/1993 | Banschick | | A01G 5/04 |
| | | | | 211/13.1 |
| 5,358,112 A * | 10/1994 | Gardner | | A61C 3/04 |
| | | | | 206/369 |
| D360,321 S | 7/1995 | Wang | | |
| 5,456,360 A * | 10/1995 | Griffin | | B01L 9/06 |
| | | | | 206/443 |
| 5,598,933 A * | 2/1997 | Lessard | | G01N 30/06 |
| | | | | 211/74 |
| D387,874 S | 12/1997 | Vila | | |
| 5,833,250 A * | 11/1998 | Schier | | B62B 1/22 |
| | | | | 280/47.19 |
| 5,993,745 A * | 11/1999 | Laska | | B01L 9/06 |
| | | | | 206/446 |
| 5,996,818 A * | 12/1999 | Boje | | B01L 9/06 |
| | | | | 206/443 |
| 6,132,684 A * | 10/2000 | Marino | | B01L 9/06 |
| | | | | 211/74 |
| 6,171,554 B1 * | 1/2001 | Kalmakis | | B01L 9/06 |
| | | | | 206/443 |
| 6,178,896 B1 * | 1/2001 | Houk, Jr. | | A47B 87/0223 |
| | | | | 108/157.13 |
| 6,193,892 B1 * | 2/2001 | Krueger | | B01L 9/06 |
| | | | | 210/695 |
| 6,250,480 B1 * | 6/2001 | McGuinness | | A47B 81/005 |
| | | | | 211/70.6 |
| D461,554 S | 8/2002 | Lafond | | |
| 6,436,351 B1 * | 8/2002 | Gubernator | | B01J 19/0046 |
| | | | | 210/257.2 |
| 6,508,369 B2 * | 1/2003 | Wang | | A47F 7/0028 |
| | | | | 211/60.1 |
| 6,568,544 B1 * | 5/2003 | Lafond | | B01L 9/06 |
| | | | | 211/74 |
| 6,663,836 B1 * | 12/2003 | Kalmakis | | B01L 9/06 |
| | | | | 235/435 |
| 7,036,668 B2 * | 5/2006 | Udy | | B25H 3/04 |
| | | | | 211/60.1 |
| 7,232,038 B2 * | 6/2007 | Whitney | | B01L 9/06 |
| | | | | 211/74 |
| D566,851 S | 4/2008 | Hawker | | |
| D591,425 S | 4/2009 | Hawker | | |
| D624,360 S * | 9/2010 | Leavelle | | D7/501 |
| D638,138 S * | 5/2011 | Wong | | D24/227 |
| 8,061,517 B2 | 11/2011 | Loeffler et al. | | |
| D659,850 S * | 5/2012 | Thom | | D24/229 |
| D683,046 S | 5/2013 | Yin | | |
| 8,505,723 B2 * | 8/2013 | Clark | | B65D 5/503 |
| | | | | 206/443 |
| 8,940,252 B2 | 1/2015 | Ziegler | | |
| D785,428 S | 5/2017 | Friesen | | |
| 9,776,188 B1 * | 10/2017 | Kamees | | B01L 9/06 |
| D814,653 S | 4/2018 | Shedlosky | | |
| 10,034,806 B1 * | 7/2018 | Greenhalgh, Sr. | | A61G 7/05 |
| D848,638 S | 5/2019 | Sims | | |
| D849,961 S | 5/2019 | Muller | | |
| D867,614 S | 11/2019 | Jones | | |
| D882,818 S | 4/2020 | Leimkuehler | | |
| 10,694,922 B1 | 6/2020 | Audibert et al. | | |
| D898,941 S | 10/2020 | Ollar | | |
| D900,337 S | 10/2020 | Kamees et al. | | |
| D902,433 S | 11/2020 | Livingston et al. | | |
| D903,901 S | 12/2020 | Griffin | | |
| D906,537 S | 12/2020 | Sims et al. | | |
| D913,753 S | 3/2021 | Zheng | | |
| 2002/0108917 A1 * | 8/2002 | Maruyama | | B01L 9/06 |
| | | | | 211/74 |
| 2002/0170867 A1 * | 11/2002 | Liu | | B01L 9/06 |
| | | | | 211/74 |
| 2003/0017084 A1 * | 1/2003 | Dale | | B01L 9/06 |
| | | | | 422/562 |
| 2003/0034317 A1 * | 2/2003 | Lafond | | B01L 9/06 |
| | | | | 211/74 |
| 2004/0188367 A1 * | 9/2004 | Pleiman | | B25H 3/04 |
| | | | | 211/70.6 |

(56) References Cited

U.S. PATENT DOCUMENTS

| | | | | |
|---|---|---|---|---|
| 2005/0165287 | A1* | 7/2005 | Wescott, III | B01L 9/06 600/322 |
| 2005/0205673 | A1* | 9/2005 | Morris | B01L 3/5027 235/385 |
| 2007/0062892 | A1* | 3/2007 | Donnellan | A47B 49/00 211/74 |
| 2007/0235395 | A1* | 10/2007 | Mondale | A46B 17/00 211/65 |
| 2008/0075634 | A1* | 3/2008 | Herchenbach | B01L 9/06 422/400 |
| 2008/0164210 | A1* | 7/2008 | DeMarco | B01L 9/06 210/656 |
| 2011/0274595 | A1* | 11/2011 | Ziegler | B01L 9/06 422/562 |
| 2012/0085720 | A1* | 4/2012 | Bettenhausen | A61L 2/26 211/85.13 |
| 2012/0175328 | A1* | 7/2012 | Bosch | B01L 9/06 211/85.18 |
| 2015/0336102 | A1* | 11/2015 | Tyagi | B01L 9/06 422/562 |
| 2016/0058249 | A1* | 3/2016 | Pitman | A47K 1/09 248/311.2 |
| 2017/0361325 | A1* | 12/2017 | Kantor | B01L 9/06 |
| 2018/0064507 | A1 | 3/2018 | Kierser et al. | |
| 2018/0116747 | A1 | 5/2018 | Matityahu et al. | |
| 2018/0206933 | A1 | 7/2018 | Healey et al. | |
| 2019/0060909 | A1* | 2/2019 | Wardenburg | B01L 9/06 |
| 2019/0070573 | A1 | 3/2019 | Akiyama | |
| 2020/0315349 | A1 | 10/2020 | Rapier et al. | |
| 2021/0094037 | A1 | 4/2021 | An et al. | |

OTHER PUBLICATIONS

Written Opinion of the International Searching Authority dated Jun. 8, 2020 in connection with PCT PCT /182020/053054.

Lab Supplies, Online, published date unknown, Retrieved on May 21, 2020 from URL: https://www.aliexpress.com/item/32843468724.

Scienceware F18745-0011 Switch-Grid Test Tube Rack, Holds 13-16mm Tubes, Blue, Cole-Parmer Scientific Experts, Downloaded May 20, 2020 from URL:www.colepalmercom/i/scienceware-f18745-0011-switch-grid-test-tube-rack-holds-13-16.

* cited by examiner

TUBE RACK APPARATUS

TECHNICAL FIELD

Example embodiments disclosed herein relate generally to the storage of medical supplies, and more specifically to the storage of shaped tube rack apparatuses and methods of making and using the same.

SUMMARY

A brief summary of various example embodiments is presented below. Some simplifications and omissions may be made in the following summary, which is intended to highlight and introduce some aspects of the various example embodiments, but not to limit the scope of the invention. Detailed descriptions of example embodiments adequate to allow those of ordinary skill in the art to make and use the inventive concepts will follow in later sections.

Embodiments include a tube rack apparatus including a bottom portion having a first length, a plurality of indents formed in the bottom portion and configured to receive tubes and keep tubes straight and restrict the movement of a bottom of the tubes, the plurality of indents exposing a lower surface of the bottom portion, a plurality of legs extending from the bottom portion, a top portion having a second length longer than the first length, a plurality of openings formed in the top portion, the plurality of openings aligned with the plurality of indents, and at least one handle member extending from a first end of the top portion.

The at least one handle member may be spaced from the plurality of openings by a distance substantially equal to a width of a row of openings.

The top portion may include hook members configured to fit into the plurality of legs of the bottom portion.

The plurality of legs may include slanted legs configured to fit into angled drawers.

At least one slanted leg may be formed of a same continuous piece as the at least one handle member. The slanted legs may extend between the bottom portion and the top portion forming an open space that is configured to stack multiple tube racks.

The top portion, bottom portion, and handle member may include rounded corners for ease of user handling.

All of the plurality of legs may extend substantially perpendicular from a flat surface of the bottom member.

A label holder may have peg elements configured to fit into the openings of the top portion. The label holder may include a flat portion and a clip portion configured to snap onto the peg element.

The top portion may include a plurality of label holder holes and an extended label holder configured to fit into the plurality of label holder holes.

The tube rack apparatus may include a plurality of label holders with different labels configured to demarcate the rack into different areas. The extended label holder may extend above the handle for easy viewing. A label may have a plurality of fields to display names, shapes, and dimensions of elements.

Tube rack labels may be affixed to the tube rack apparatus. The tube rack labels may include color coded fields to identify at least one of part type, part image, and a dimension of the part.

The part type may be a screw. The dimension may be a diameter. The color coded fields of the tube rack may be consistent with other tube rack apparatus labels including one of cabinet label, drawer label, and tube labels.

Labels may be configured to be affixed to a plurality of tubes.

BRIEF DESCRIPTION OF THE DRAWINGS

Additional objects and features of the invention will be more readily apparent from the following detailed description and appended claims when taken in conjunction with the drawings. Although several example embodiments are illustrated and described, like reference numerals identify like parts in each of the figures, in which:

DETAILED DESCRIPTION

Figure 1:
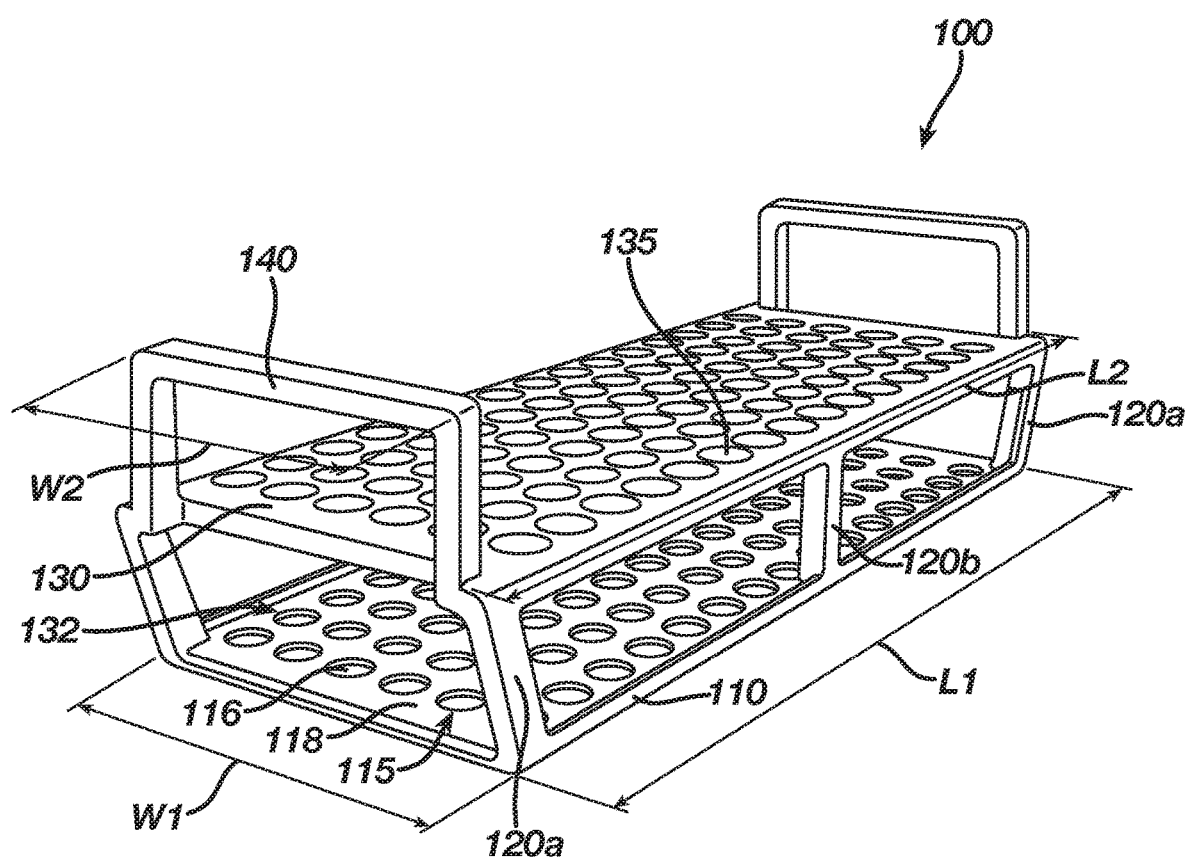
FIG. 1 illustrates a tube rack apparatus in accordance with example embodiments described herein.

It should be understood that the figures are merely schematic and are not drawn to scale. It should also be understood that the same reference numerals are used throughout the figures to indicate the same or similar parts.

The descriptions and drawings illustrate the principles of various example embodiments. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various example embodiments described herein are not necessarily mutually exclusive, as some example embodiments can be combined with one or more other example embodiments to form new example embodiments. Descriptors such as "first," "second," "third," etc., are not meant to limit the order of elements discussed, are used to distinguish one element from the next, and are generally interchangeable. Values such as maximum or minimum may be predetermined and set to different values based on the application.

In the art, many companies use sterile packed implants that include screws, plates, etc. Though transferring screws to sterile packaging has benefits for traceability and safety, challenges remain. Users have difficulty storing various types of screws. Space in hospitals is limited and a solution is needed to make the storage of screws as efficient and effective as possible. Inventory and nursing staff struggle to find a correct implant. Poor labeling, organization and inconsistency cause hospital staff to misplace product, open the wrong product, or even implant the incorrect product. Using the racks and labelling systems described herein, sterile tube packaging may enter a hospital or care environment and seemlessly integrate into their existing systems.

A sterile tube system to be used in a hospital or care environment may include one or more cabinets to store various drawers. The drawers may include many types of medical supplies. In order to distinguish one type of medical supply product from another, labels may be placed on different drawers in the cabinet. One or a plurality of drawers may include tube racks as described herein. The tube racks may include tubes that house various types of screws or other items to be used in medical and surgical procedures. Various parts of the tube racks and the individual tubes may carry labels that provide information to distinguish contents of racks and tubes from each other.

FIG. 1 illustrates a tube rack apparatus 100 in accordance with example embodiments described herein. The tube rack apparatus 100 may be made up of a bottom portion 110 having a first length L1 and a first width W1. Within the bottom portion 110 may be a plurality of indents 115. The plurality of indents 115 may be formed within the bottom portion 110 and configured to receive tubes (such as tubes 1340 illustrated in FIGS. 13C and 13D) and keep the tubes straight and restrict movement of the of the end of the tube in indents 115. The plurality of indents 115 may expose a lower surface 116 of the bottom portion 110 that is different than an upper surface 118 of the bottom portion 110. The plurality of indents 115 are holes that are formed between the upper surface 118 and the lower surface 116. The plurality of indents 115 do not extend through the lower surface 116 of the bottom portion 110 and therefore any tubes placed in the tube rack apparatus 100 will not extend through the bottom portion 110.

As illustrated in FIG. 1, a plurality of legs are configured to extend from the bottom portion 110. The plurality of legs may include slanted legs 120a and perpendicular legs 120b that are positioned substantially perpendicular to a flat surface of the bottom portion 110. The plurality of legs 120a and 120b may connect to a top portion 130 of the tube rack apparatus 100. The top portion 130 may have a second length L2 that is longer than the first length L1 of the bottom portion 110. Because of the longer length, the top portion 130 may extend past both sides of the the bottom portion HO. The difference in lengths L2 and L1 on either side of the tube rack apparatus 100 leaves an open space 132 configured to stack one tube rack apparatus 100 on top of another and to accommodate a handle from a lower tube rack apparatus 100.

The top portion 130 includes a plurality of openings 135. The plurality of openings 135 may be vertically aligned with the plurality of indents 115, to receive and hold a plurality of tubes 1340. Attached to the top portion 130 may be at least one handle member 140. Handle members 140 may be used to lift the tube rack apparatus 100 in or out of a drawer 1320 (illustrated in FIG. 13B) or move about a medical facility. Drawers 1320 may have a particular depth or limited space in which a user such as a medical worker may access the tube rack apparatus 100. The handles 140 may facilitate easy access to the tube rack apparatuses 100 and the contents therein.

The at least one handle member 140 may have a width W2 smaller than a width W1 of the bottom portion 110. The width W1 may also be a width of the top portion 130. The width W2 of the handle member 140 is configured in order to facilitate stacking of multiple tube rack apparatuses 100. From below, a handle member 140 will fit into the open space 132. A pair of handle members 140 may be used to lift the tube rack apparatus 100 and move it from one location to another, such as into and out of a drawer or rack cabinet, a shelf, medical procedure space, or below or on top of another tube rack apparatus 100.

Figure 2:
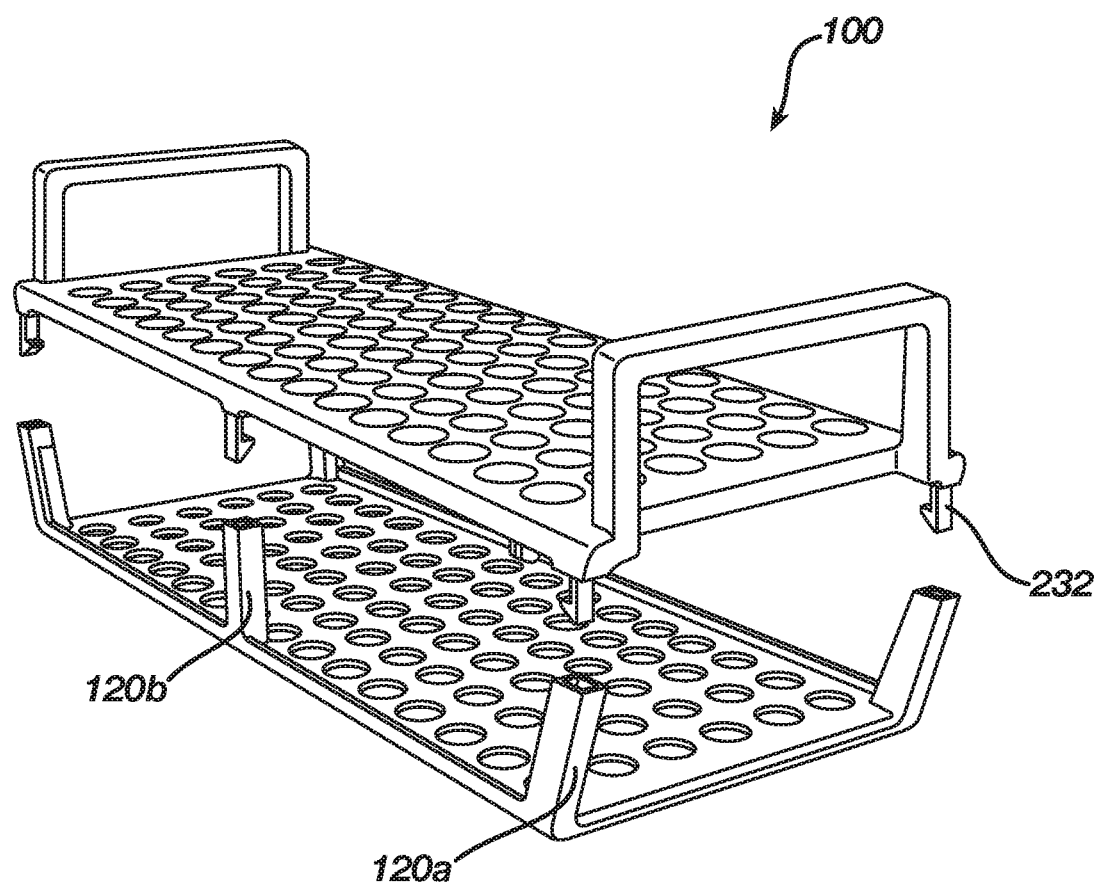
FIG. 2 illustrates a disassembled view of the tube rack apparatus in accordance with FIG. 1.

FIG. 2 illustrates a disassembled view of the tube rack apparatus 100 in accordance with FIG. 1. As illustrated in FIG. 2, the plurality of legs 120a and 120b are configured to extend from the bottom portion 110 towards the top portion 130. The plurality of legs 120a and 120b may be formed of one continuous piece with the bottom portion 110. A material for the tube rack apparatus 100 may be plastic, polymer, or other materials as known in the art. The top portion 130 may include hook members 232 that are configured to fit into the plurality of legs 120a and 120b of the bottom portion 110. In other embodiments, the legs 120a and 120b may be formed of one continuous piece with the top portion 130, and the bottom portion 110 may include the hook member that are configured to fit into the plurality of legs 120a and 120b. Further, other connection mechanisms may be used to connect the bottom portion 110 and 130.

As illustrated in FIGS. 1 and 2, the plurality of legs may include slanted legs 120a at distal ends of the tube rack apparatus 100, and substantially perpendicular legs 120b at a middle portion of the bottom portion tube rack apparatus 100. The slanted legs 120a may be so configured as to fit into angled drawers such as drawers 1320

Figure 3:
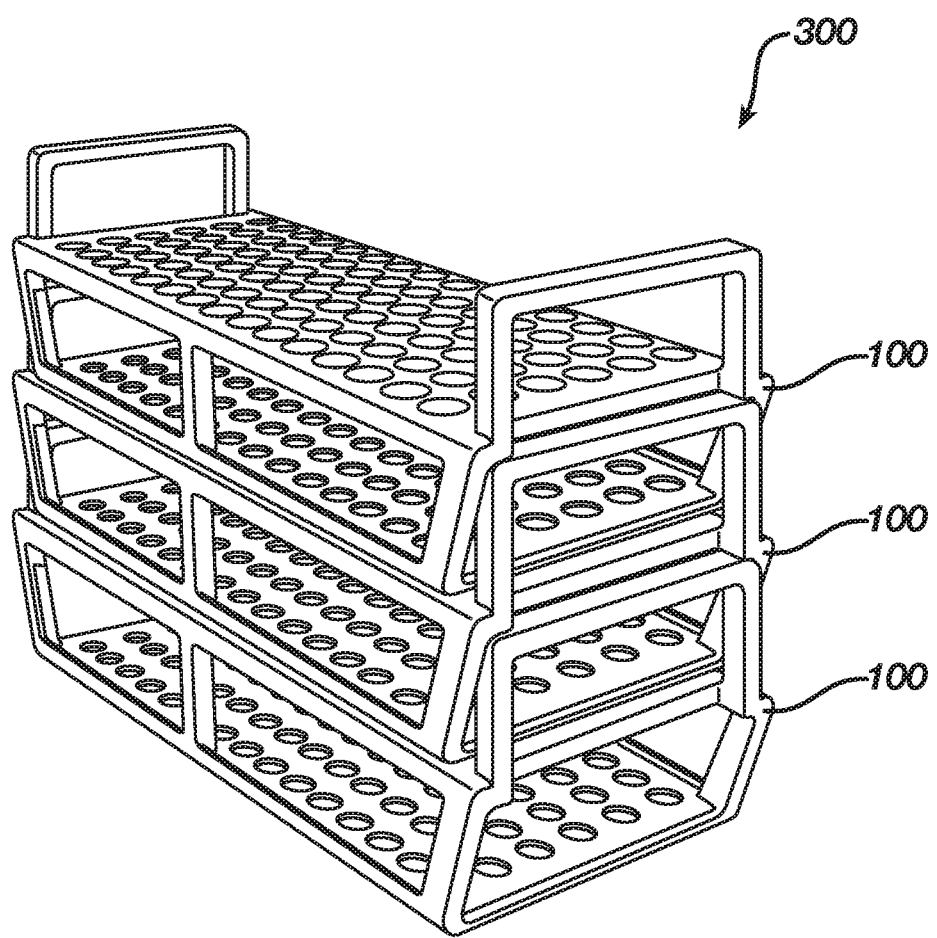
FIG. 3 illustrates multiple tube rack apparatuses in a stacked configuration in accordance with FIG. 1.

FIG. 3 illustrates multiple tube rack apparatuses 100 in a stacked configuration 300 in accordance with FIG. 1. The stacked configuration 300 may be used when the tube rack apparatuses do not have tubes inserted therein, or when tubes are only inserted into a top tube rack apparatus 100. As described herein, the slanted legs 120a may extend between the bottom portion 110 and the top portion 130 forming the open space 132 (illustrated in FIG. 1) that is configured to receive a handle member 140 of subordinate tube rack apparatus 100. The handle members 140 have the smaller width W2 configured to fit within the open spaces 132.

Because the tube rack apparatuses 100 may be handled by human hands, including the placing and removal of tubes, the edges of all tube rack apparatus 100 surfaces including the bottom portion 110, plurality of legs 120a and 120b, top portion 130, and handle member 140 may have smoothed and rounded corners for ease of handling.

Figure 4:
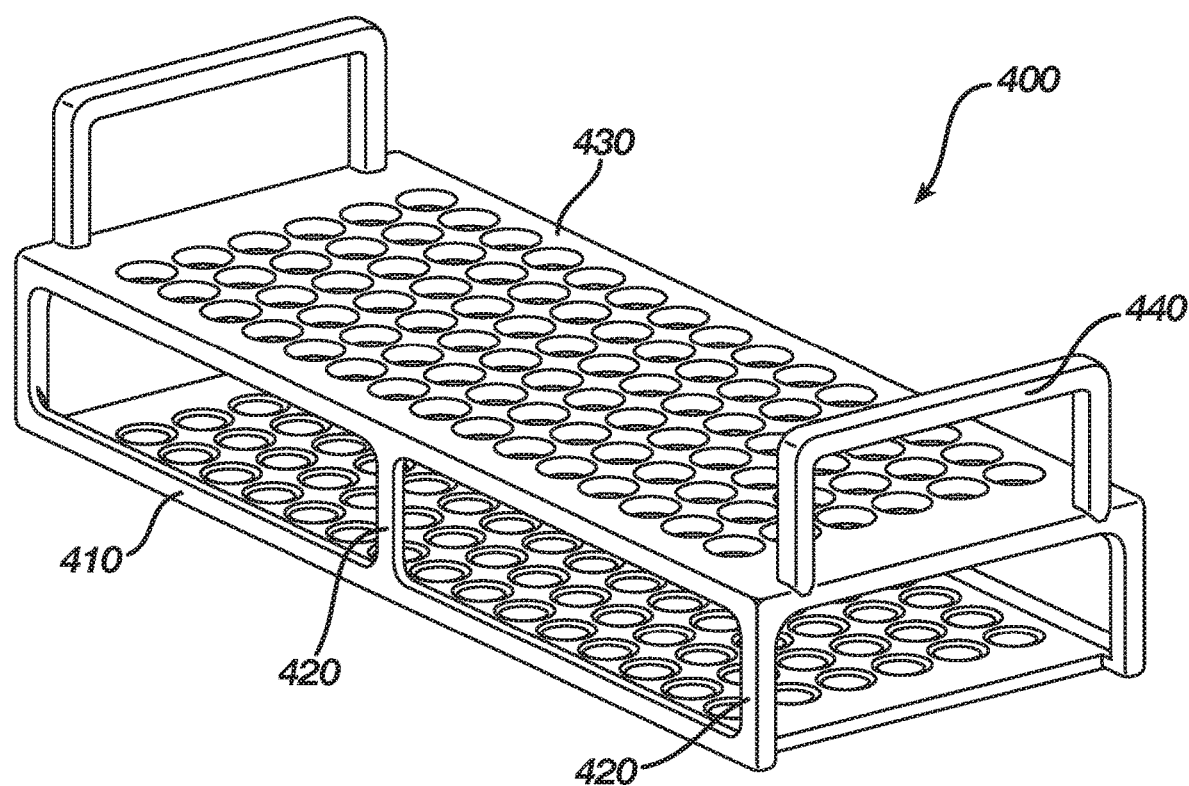
FIG. 4 illustrates an example embodiment of a tube rack apparatus in accordance with example embodiments described herein.

FIG. 4 illustrates an example embodiment of a tube rack apparatus in accordance with example embodiments described herein. In FIG. 4, a tube rack apparatus 400 may be configured to have all legs 420 extending between a bottom portion 410 and a top portion 430 to be substantially perpendicular to the bottom portion 410 and top portion 430. In the example embodiment of FIG. 4, a width of a handle member 440 may be smaller than a width of the bottom portion 410 and top portion 430, to allow tube rack apparatuses 400 to be stacked one on top of another.

Figure 5:
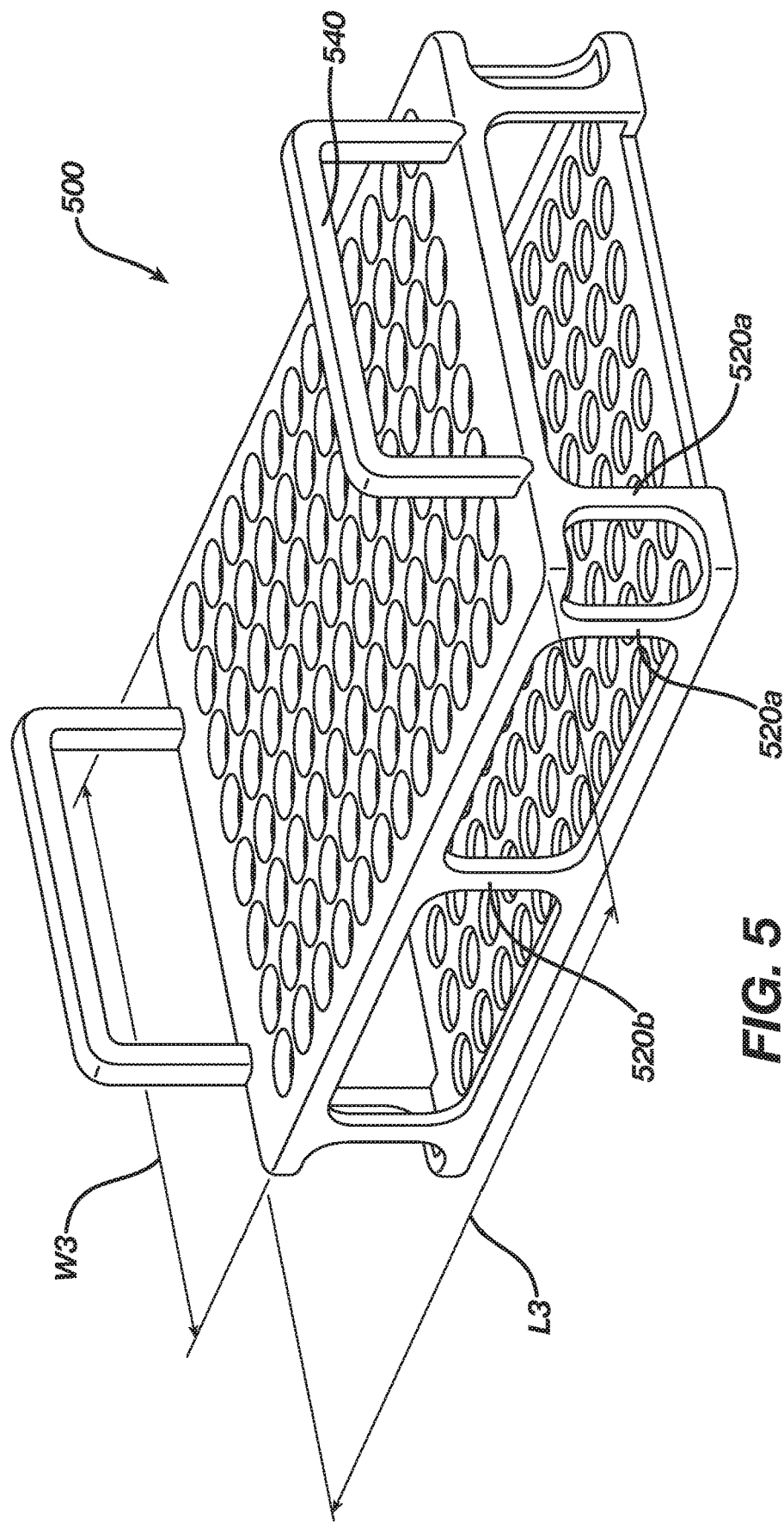
FIG. 5 illustrates a tube rack apparatus having a wide width and short length in accordance with example embodiments described herein.

FIG. 5 illustrates a tube rack apparatus 500 having a wide width W3 and short length L3 in accordance with example embodiments described herein. The dimensions are not limited to what is illustrated. Length and wide dimension of tube rack apparatuses described herein may be designed to have various lengths and widths to meet customer or design requirements. In addition to middle legs 520b, the tube rack apparatus 500 may include a plurality of corner legs 520a to provide more stability when a larger side tube rack apparatus is designed and built. Similar to other designs, a width of a handle member 540 is kept smaller than a width separating two legs, allowing a stackable configuration of tube rack apparatuses 500. Tube rack apparatus may be manufactured that are narrow such that two or more racks may be inserted within a drawer. For example, four racks as shown in FIG. 4 may be placed in a drawer side by side (along the width direction). In another example, four racks as shown in FIG. 5 may be arranged in a rectangular configuration, where the four racks are arranged in a 2×2 formation.

Figure 6:
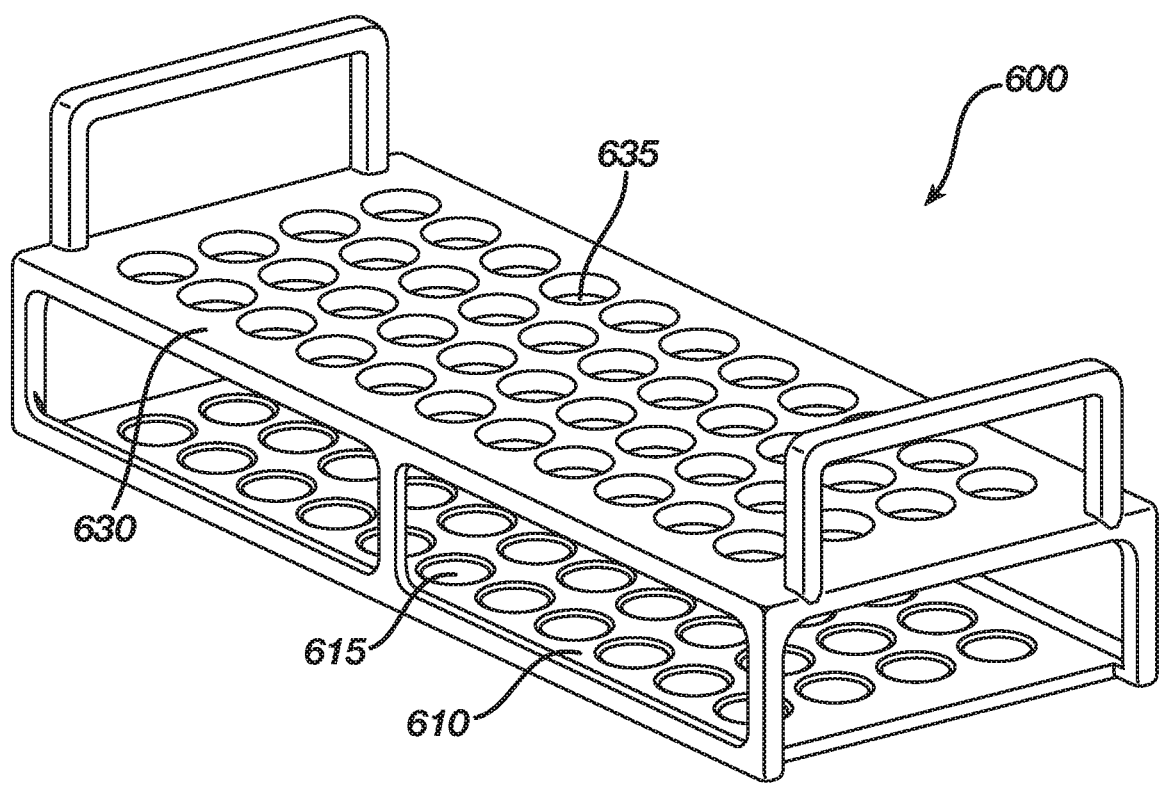
FIG. 6 illustrates a tube rack apparatus in another configuration in accordance with example embodiments described herein.

FIG. 6 illustrates a tube rack apparatus 600 in another configuration in accordance with example embodiments described herein. The tube rack apparatus 600 may include a bottom portion 610 and a top portion 630 that have larger indents 615 and larger holes 635 than other example embodiments. In fact, tube rack apparatuses in accordance with example embodiments may be designed to have the diameter sizes of top portion holes and bottom portion indents various sizes in response to customer or design demand.

Figure 7:
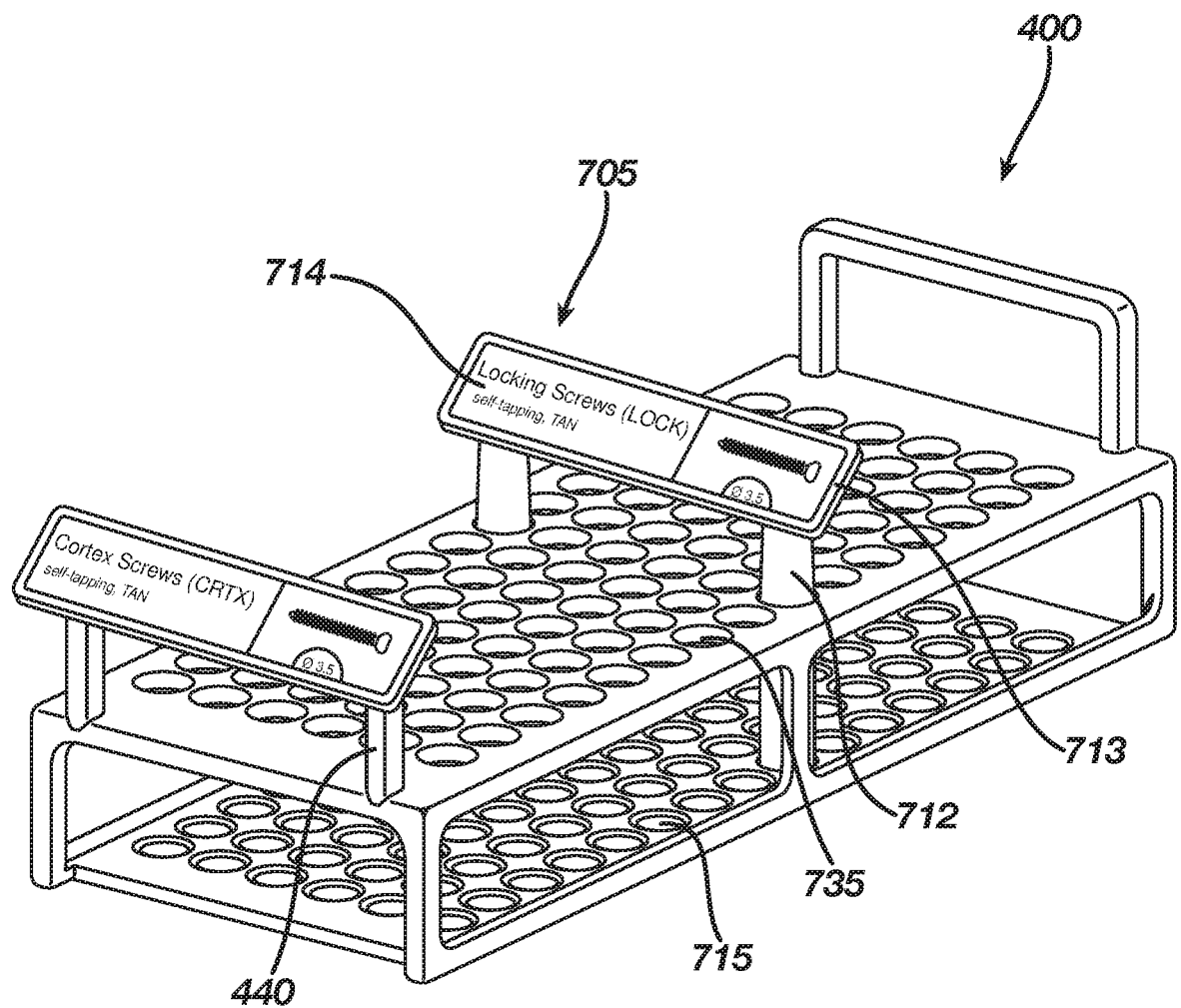
FIG. 7 illustrates a label holder system in accordance with embodiments described herein.

FIG. 7 illustrates a label holder system 705 in accordance with embodiments described herein. The label holder system 705 may be used with a tube rack apparatus such as tube rack apparatus 400 of FIG. 4, but label holder systems 705 are not limited thereto. Label holder systems 705 as illustrated and described with regard to FIG. 7 may be used in other tube rack apparatuses of the present application. The label holder system 705 may include a peg component 712 including two pegs jointed by a label holder 713. The two pegs are vertical members that extend through openings 735 and fit snugly into indents 715. The pegs may have a diameter substantially the same from bottom to top, or may have a diameter that tapers towards a top of the pegs. A label 713 may be affixed to the label holder 713. The peg components 712 may be inserted into openings 735. The label 714 may be affixed in various ways to the label holder 713. A label 714 may also be affixed to various handles 440 of the tube rack apparatus 400. A tube rack apparatus 400 may use labels 714 atop handle members 440 and label holder systems 705 to demarcate different sections of the tube rack apparatus 400. For example, a first area of the tube rack apparatus 400 may include cortex screws of a particular type, material, and size.

A second area of the tube rack apparatus 400 may include locking screws of a particular type, material, and size. Embodiments are not limited to two areas of demarcation, and may include multiple areas designated by a plurality of label holder systems 705 with or without additional labelling on a handle member 440.

Figure 8:
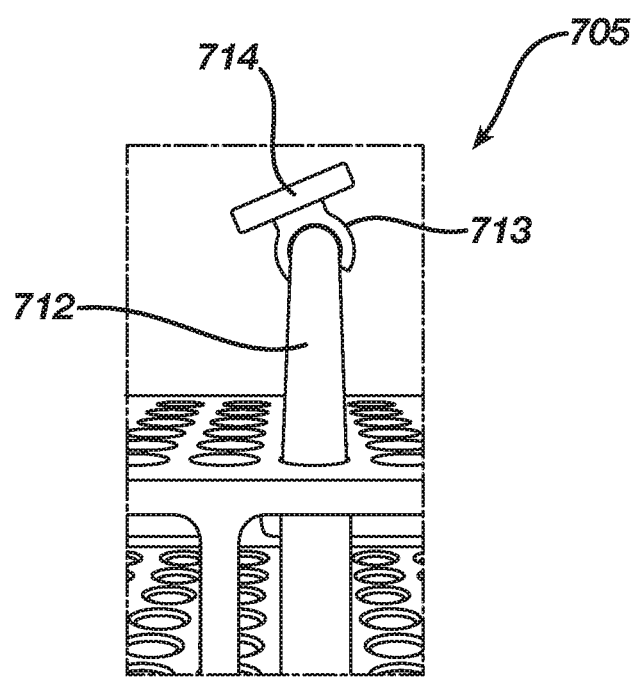
FIG. 8 illustrates a side view of the label holder system in accordance with FIG. 7.

FIG. 8 illustrates a side view of the label holder system 705 in accordance with FIG. 7. The label holder 714 may be flat and have a snap or clip member 713 configured to connect the label holder 714 to the peg component 712. The snap member 713 may be rounded to affix to a round part of the peg component 712, or may be rectangular or other shape to snap onto a handle member 440. Other affixing parts may be used to affix the label holder 714 to the peg component 712 such as Velcro, stickers, temporary glue, or other mechanical means of fixation. The label holder 714 may provide an indentation for interchangeable labels used to identify contents of various tubes. The snap member may curve around the peg component 712 to adjust an angle of view of the label holder 714.

Figure 9A:
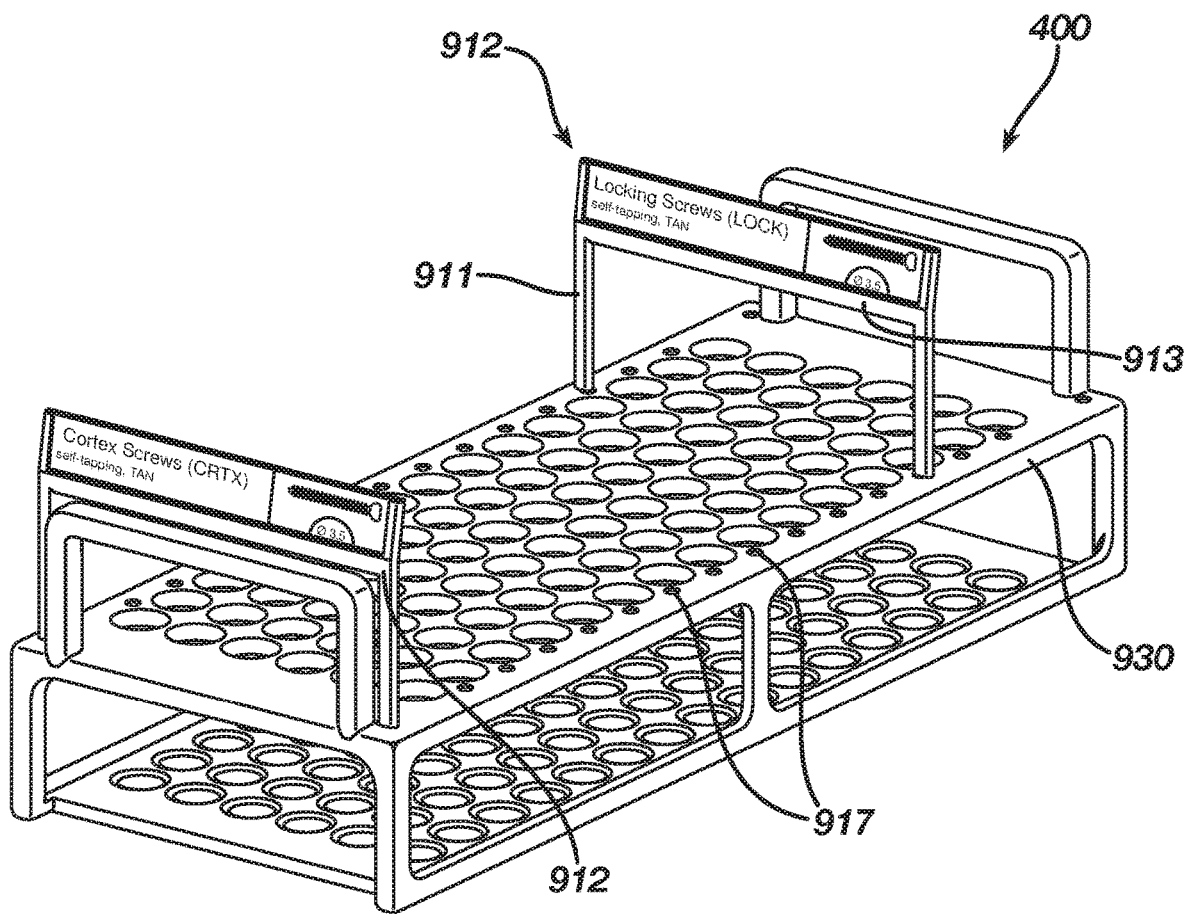
FIG. 9A illustrates an extended label holder in accordance with example embodiments described herein.

FIG. 9A illustrates an extended label holder 912 in accordance with example embodiments described herein. The extended label holder 912 may include a pair of thin posts 911 connected by a label section 913. The thin posts 911 may have perimeters that are smaller than perimeters of the handle members. Instead of placing peg components into tube openings in the top portion 930, the extended label holders 912 may be inserted into a plurality of label holder holes 917 disposed adjacent edges of the top portion 930. Into the label holder holes 917 may be placed the extended label holders 912. The extended label holders 912 are configured to rise higher than handle members 440 such that the extended label holders 912 provide high labels for easy viewing. There may be multiple extended label holders 912 placed within a rack to demarcate a plurality of different components stored in different tube areas.

Figure 9B:
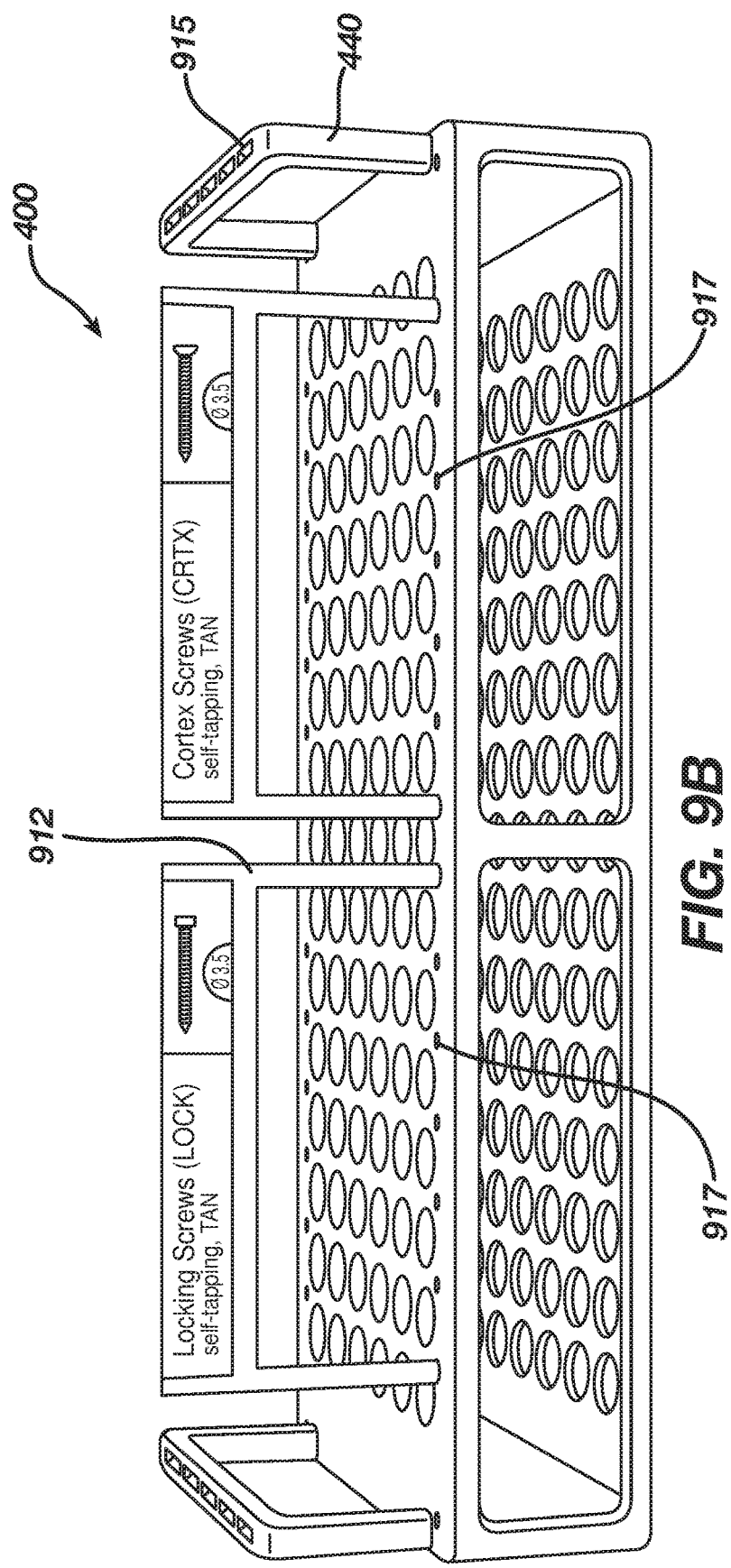
FIG. 9B illustrates another placement for the extended label holder in accordance with example embodiments described herein.

FIG. 9B illustrates another placement for the extended label holder 912 in accordance with example embodiments described herein. As illustrated in addition to extended label holders 912 being placed across a length of a top portion 910, extended label holders 912 illustrated in FIG. 9B may be placed on along a side of the top portion 910. Multiple extended label holders 912 may be placed in label holder holes 917 and used to demarcate different areas of the tube rack apparatus 400. As indicated in FIG. 9B, handle members 440 may have indentations 915 formed therein. The indentations 915 may provide surface variation to a handle member 440 which is configured to aid in gripping the tube rack apparatus 400.

Figure 9C:
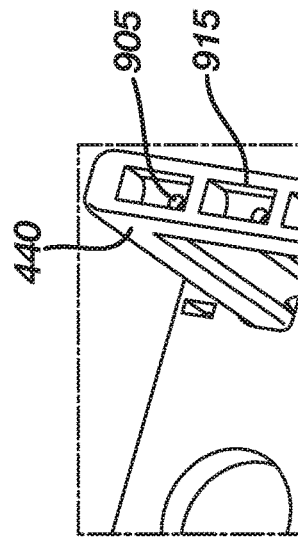
FIG. 9C illustrates indentations 915 having drainage holes 905 in accordance with example embodiments described herein.

FIG. 9C illustrates indentations 915 having drainage holes 905 in accordance with example embodiments described herein. The indentations 915 may include drainage holes 905 to prevent water or other liquids from pooling in the indentations 915 after cleaning the tube rack apparatus 400. Other handle members as illustrated and described herein may also have indentations and drainage holes.

Figure 10:
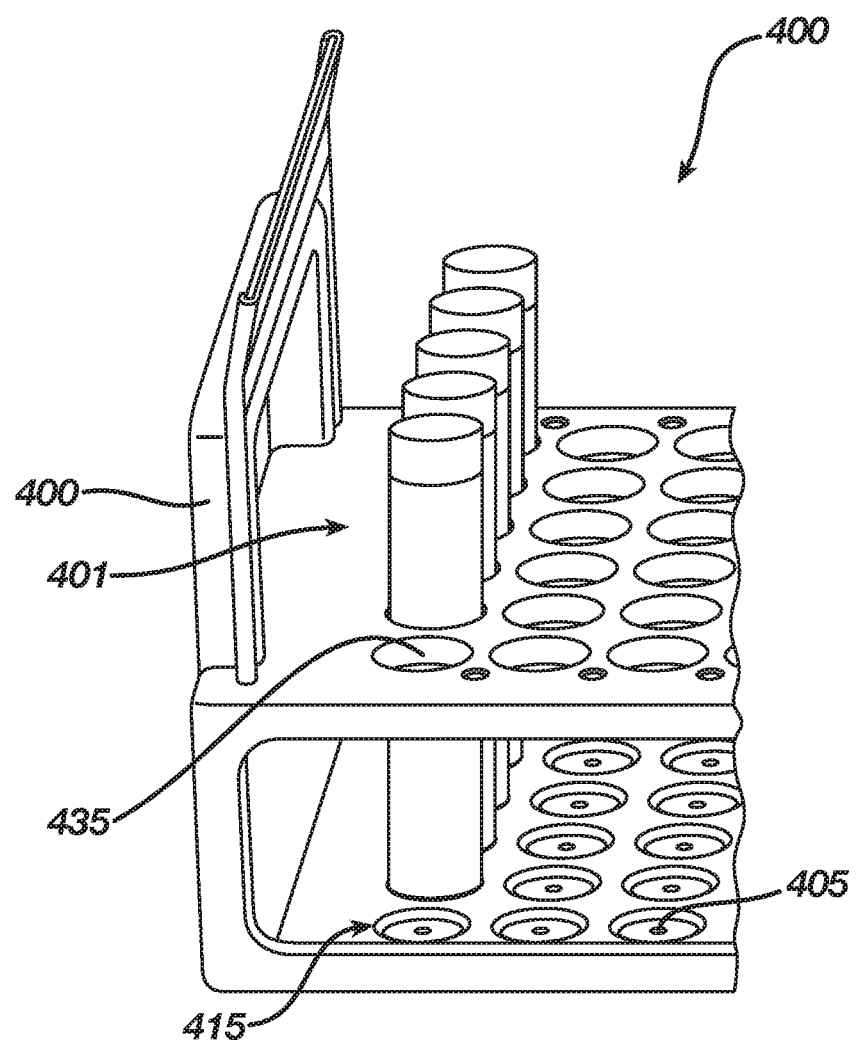
FIG. 10 illustrates a detail of a tube rack apparatus in accordance with example embodiments described herein.

FIG. 10 illustrates a detail of a tube rack apparatus 400 in accordance with example embodiments described herein. The tube rack apparatus 400 and other tube rack apparatuses illustrated and described herein may have drainage holes 405 formed in indents 415. The drainage holes 405 may prevent water or other liquids from pooling up in the indents 415 after cleaning of the tube rack apparatus 400. Between a handle member 440 and a first row of tubes may be disposed a clearance space 401. This clearance space 401 is designed to allow a user such as a medical worker grab the handle member 440 from the inside or outside of the tube rack apparatus 400 and not disturb the row of tubes. The clearance space 401 also allows a user to access the handle members 440 and remove the tube rack apparatuses from a storage drawer. A width of the clearance space 401 along the top portion 430 of the tube rack apparatus 400 may be substantially equal to a width of a row of openings 435.

Figure 11:
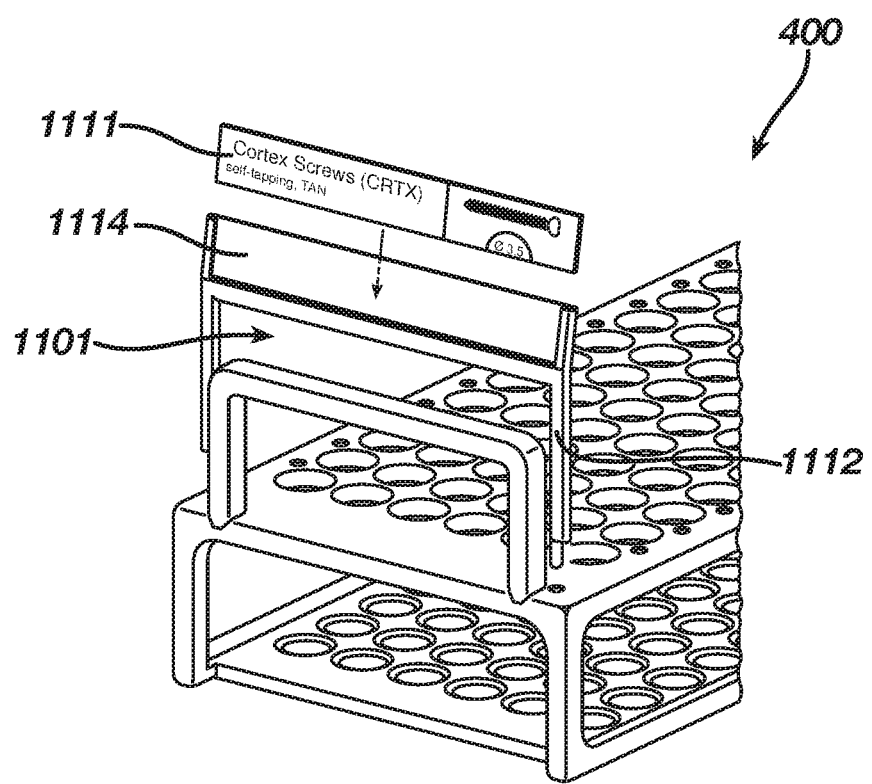
FIG. 11 illustrates a variation of the extended label holder in accordance with FIG. 9.

FIG. 11 illustrates a variation of the extended label holder in accordance with FIG. 9. Example embodiments include an ability to provide taller extended label holders 1112 to higher heights enabling a user to more readily see contends of a tube rack apparatus. Thus, a larger space 1101 may be formed between a handle 440 and a label holder 1114. Labels 1111 to be affixed to the label holders described herein may include different fields including names, shapes, and dimensions of elements deposited in label holders 1114. Labels may also be used to provide similar information on tubes.

In the various label holders, the labels may be inserted from the top or from the side to allow for easy initial labelling or for later changing the label.

Figure 12:
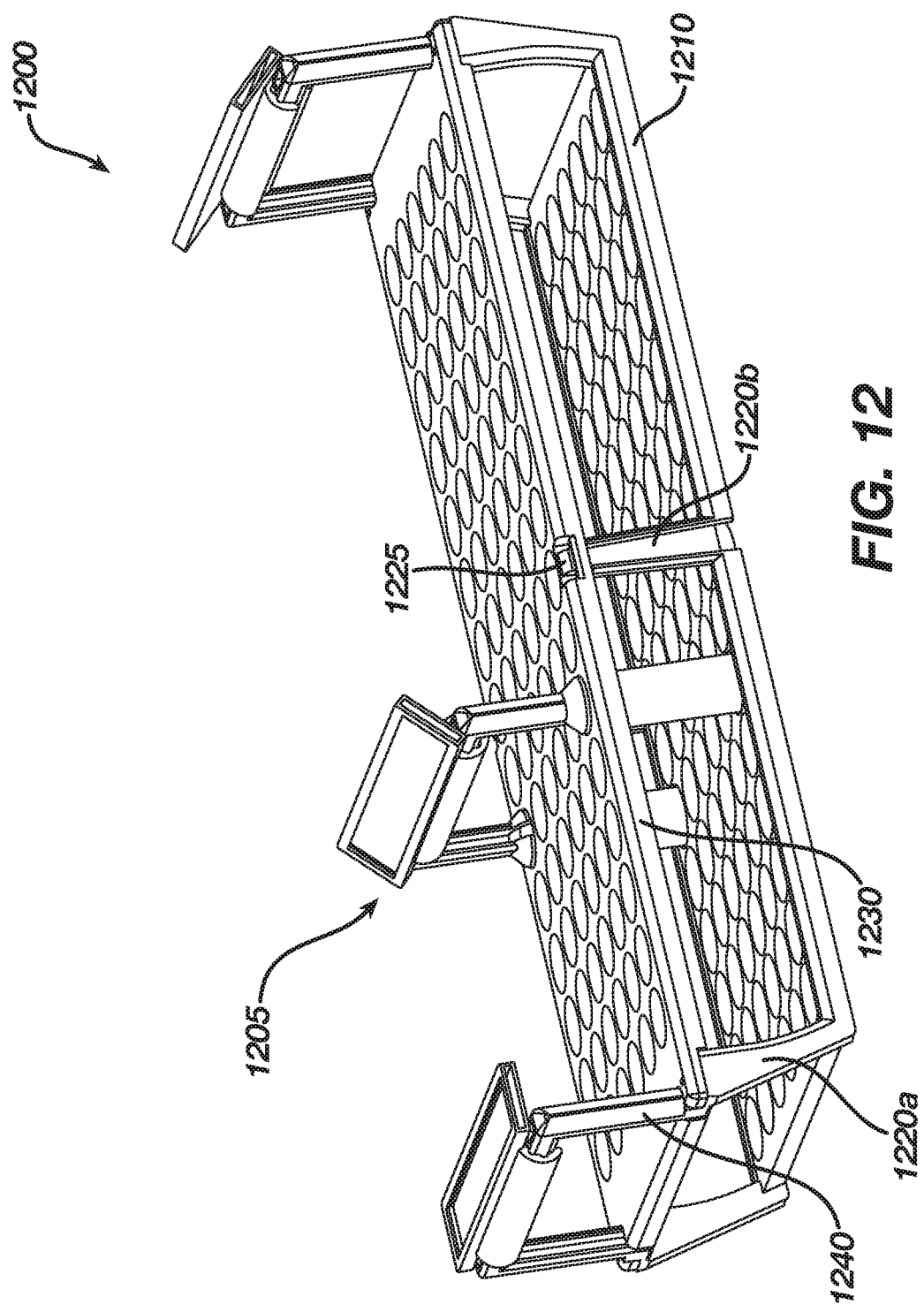
FIG. 12 illustrates another example embodiment of a tube rack apparatus in accordance with example embodiments described herein.

FIG. 12 illustrates another example embodiment of a tube rack apparatus 1200 in accordance with example embodiments described herein. FIG. 12 includes additional variations that may be used with the different tube rack apparatuses described herein. Similar to others, the tube rack apparatus 1200 may include slanted legs 1220a on opposing ends thereof. In this example embodiment, the handle members 1240 may be formed continuously, being a part of the slanted legs 1220a. Alternatively, the handle members 1240 could be part of the top portion 1230. The tube rack apparatus 1200 includes middle legs 1220b, substantially perpendicular to the top portion 1230 and bottom portion 1210. The bottom portion 1210 includes the middle legs 1220b that end in a hook member 1225 that clips to the top portion 1230. Label holders 1205 are illustrated that have the peg and snapping label arrangement, and label holders having extended labels could also be used.

Figure 13A:
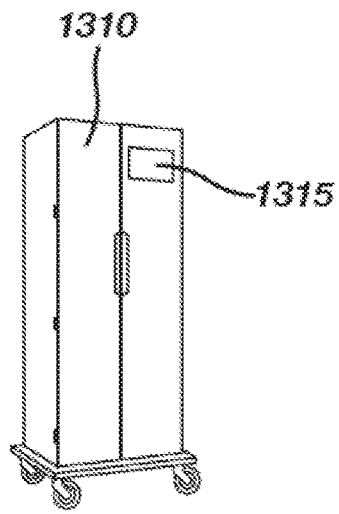
FIGS. 13A-13F illustrate various labelling systems in accordance with embodiments described herein.
Figure 13B:
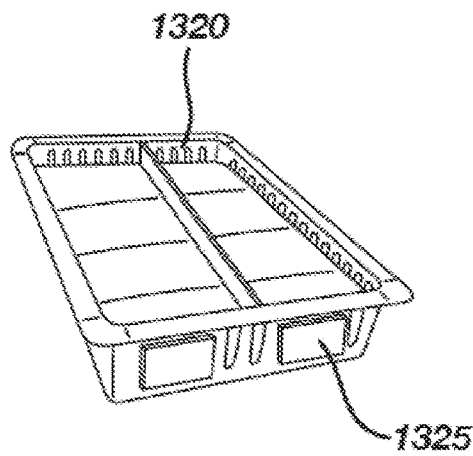
Figure 13C:
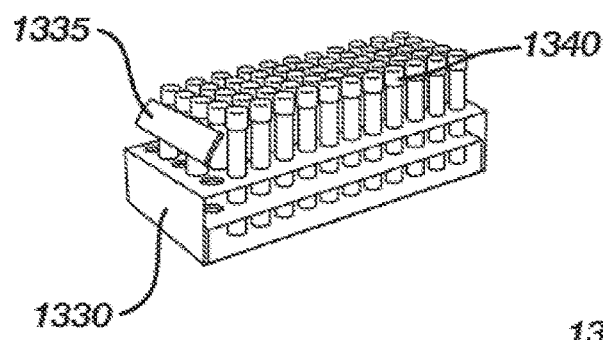
Figure 13D:
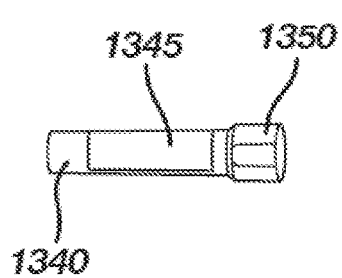
Figure 13E:
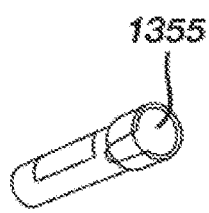
Figure 13F:
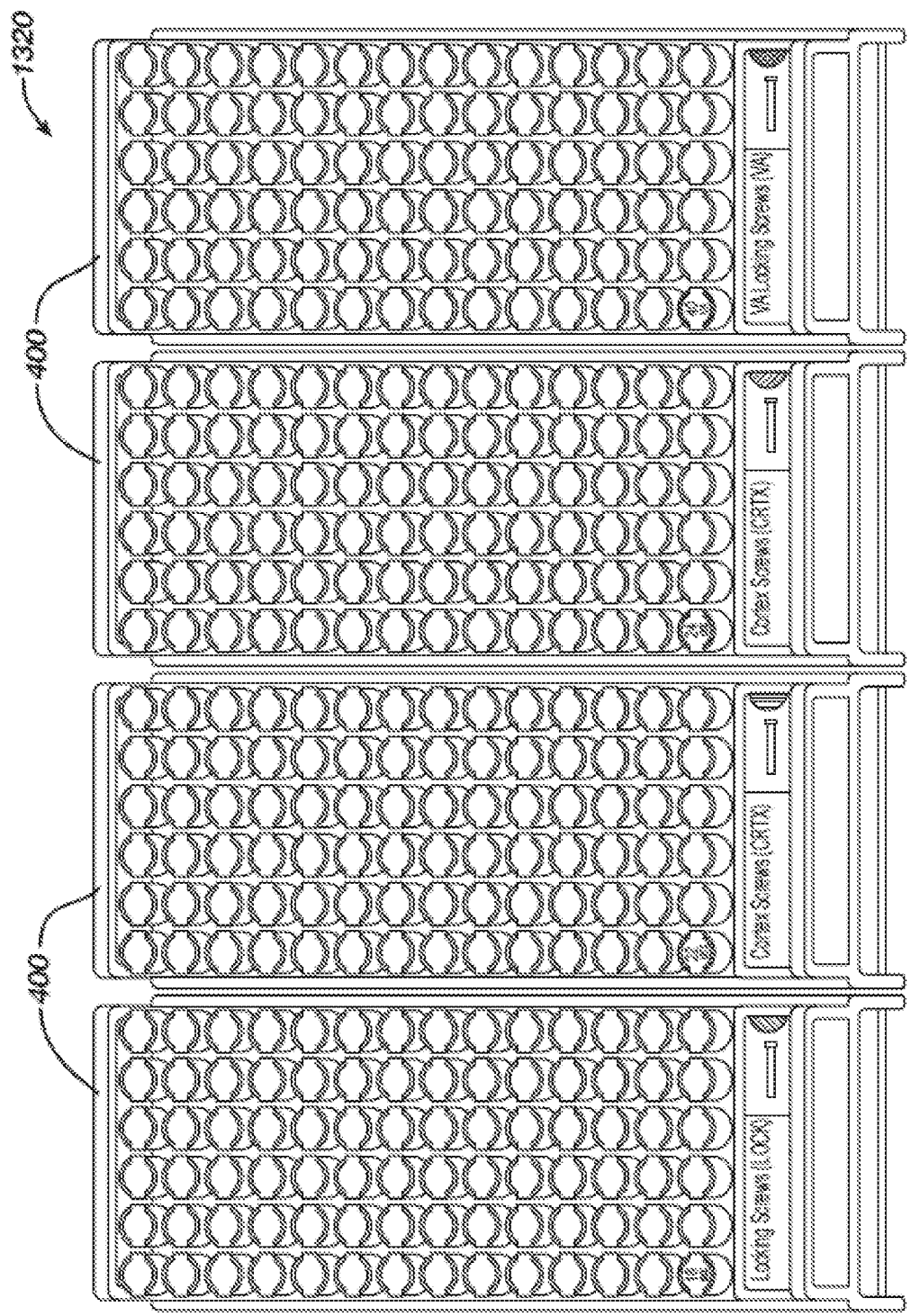

FIGS. 13A-13F illustrate various labelling systems in accordance with embodiments described herein. In FIG. 13A, a cabinet 1310 may include various label locations such as a cabinet label 1315 positioned at a top right corner of the cabinet 1310, but example embodiments are not limited thereto. The cabinet label 1315 may be placed on various parts of the cabinet as desired by a user. In FIG. 13B, the drawer 1320 may a be drawer that is configured to hold a plurality of tube rack apparatuses such as two or four, or may hold a single tube rack apparatus. FIG. 13F illustrates contents of a drawer configured to hold four tube rack apparatuses 400 in accordance with embodiments described herein. Depending on the number of tube rack apparatuses, drawer labels 1325 may be placed on external surfaces thereof. Tubes with numerical labels 18 LOCK, 22CRTX, 24 CRTX, 40 VA, and the like may fill up an entire space as illustrated or be mixed within a designated space.

FIG. 13C illustrates a tube rack apparatus 1330 as described herein. The tube rack apparatus 1330 may include a plurality of tubes 1340. A label holder system may include one or more tube rack labels 1335 at various points along the tube rack apparatus 1330 to demarcate and designate different elements present in different tubes. FIGS. 13D and 13E illustrate tubes 1340 with different types of labels thereon. A regulatory tube label 1345 on a tube 1340 may be a body label that surrounds or partially surrounds the tube 1340. A cap label 1355 may be attached to a cap 1350 of the tube 1340. The cap label 1355 may allow a user to quickly ascertain an identification of contends of a tube.

All of the labels discussed herein may include various types of information to allow a user to quickly and easily identify contents of cabinets, drawers, tube rack apparatuses, and tubes. The cabinet labels 1315, drawer labels 1325, tube rack labels 1335, regulatory tube labels 1345, and cap labels 1355 may be designed to have different fields representing consistent information on each label. Studies were conducted throughout many groups of healthcare workers and medical personnel to determine the types of information to display on the labels, as well as how to present the information in an efficient manner for quick identification, use, and return of unused tubes a designated area.

Figure 14:
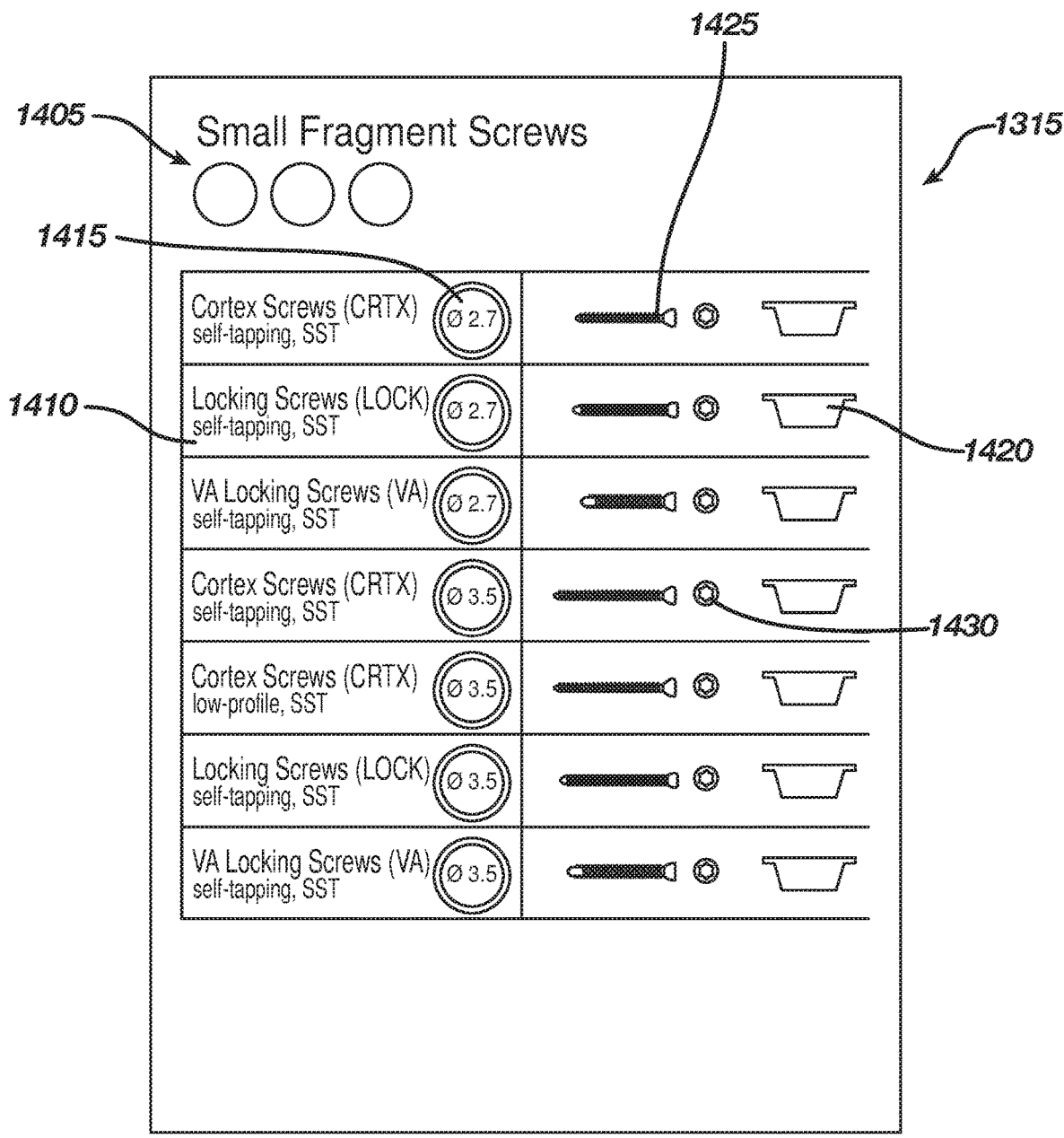
FIG. 14 illustrates an example cabinet label in accordance with example embodiments described herein.

FIG. 14 illustrates an example cabinet label 1315 in accordance with example embodiments described herein. The cabinet label may include dimension and identifying information 1405 of the types of screws or other parts such as plates that may be stored in the cabinet 1310. The cabinet label 1315 includes images of drawers 1420 to indicate that each of the screw types of each row may be found in a different drawer. The other fields on the cabinet label 1315 including part name 1410, part diameter 1415, image of part 1425, and driver type 1430 are consistent fields on other labels including drawer labels 1325, tube rack labels 1335, regulatory tube labels 1345 and cap labels 1355. Thus, a cabinet label may include information including screw diameter and color, screw type abbreviations, product pictures, product system (small frag), screw recess, drawer location, and company logo.

Part name 1410 fields may include descriptions such as "Cortex Screws (CRTX), self-tapping, SST" having a first color. Another field could be "Locking Screws (LOCK), self-tapping, SST," having a second color. SST referring to stainless steel. Other screw labels could include materials such as titanium. Cabinet labels are not limited to screw types. Other cabinet labels could identify implant types such as plates and other parts.

The part name includes the circular field 1415 that identifies the part diameter of the screw type. The diameter will have a fixed color that is consistent across all labels. The part images 1425 of each screw will be consistent, as well as a shape designating the driver type 1430 to be used to insert a screw. All of this information will be readily used by personnel as they approach a cabinet and determine which parts they need for a particular procedure.

Figure 15:
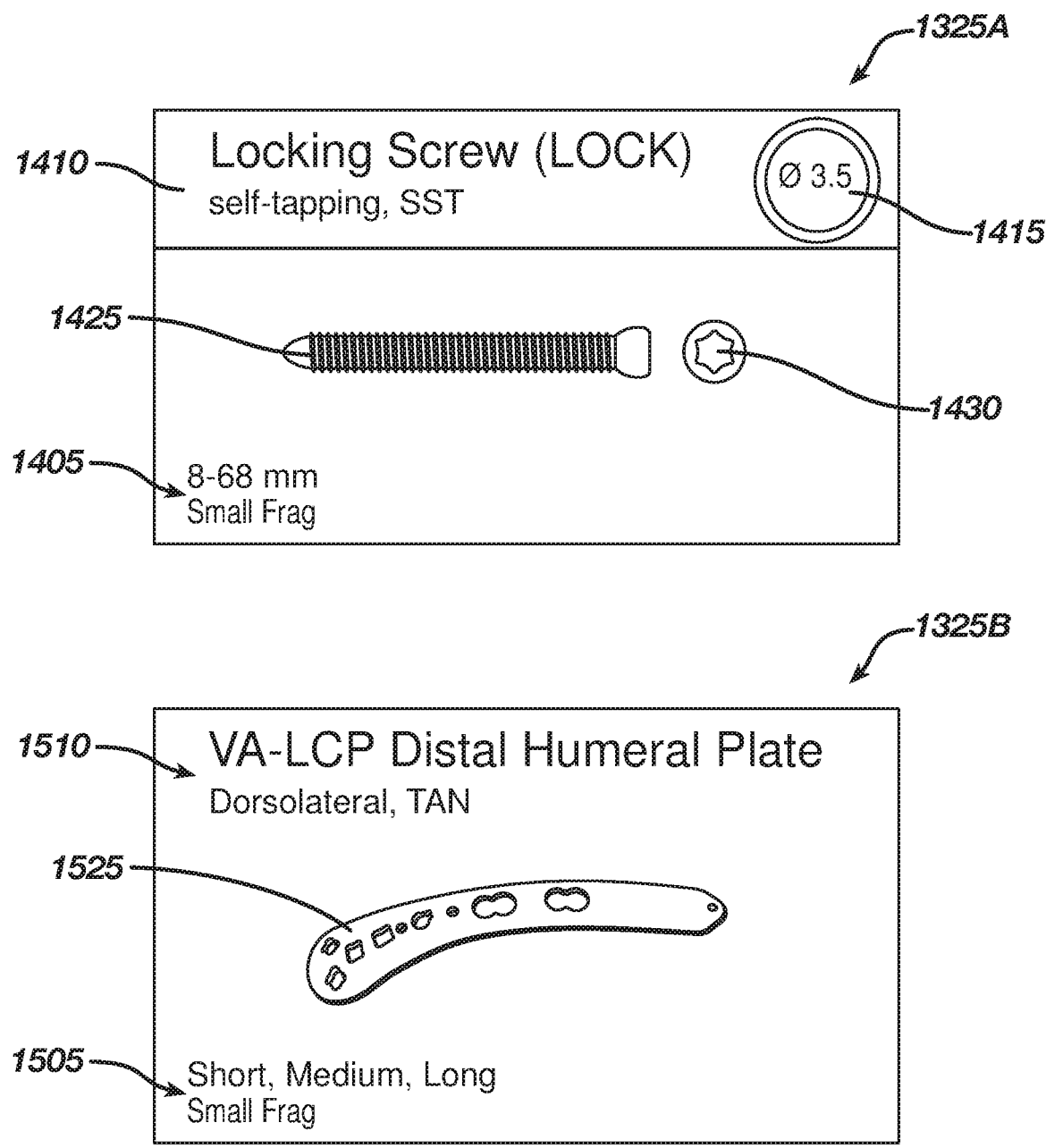
FIG. 15 illustrates examples of drawer labels in accordance with embodiments described herein.

FIG. 15 illustrates examples of drawer labels 1325A and 1325B in accordance with embodiments described herein. As noted, a drawer label 1325A such as "Locking Screw (LOCK), self-tapping, SST" shares many of the same data fields and color schemes as the cabinet label 1315, including part name 1410, part diameter 1415, part image 1425, and driver type 1430. The label may include other dimension and identifying information 1405. Another type of drawer label 1325B includes a type of plate to be used in different procedures having an identifying field 1510, image field 1525, and other identifying information 1505. A drawer label may thus include information including screw type, screw type abbreviation, screw diameter and color, screw information (as needed), product picture, screw recess, screw length, product system (small frag), and company logo.

Figure 16:
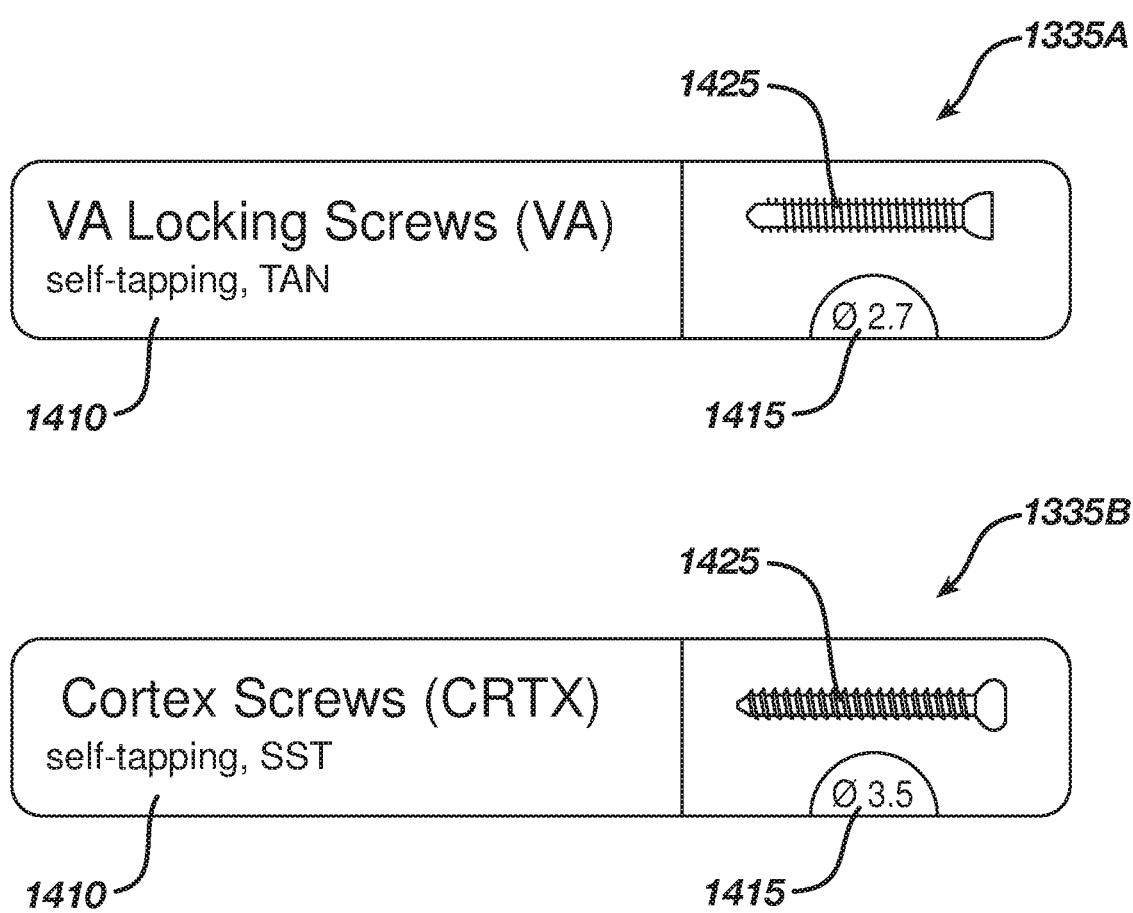
FIG. 16 illustrates examples of tube rack labels in accordance with example embodiments described herein.

FIG. 16 illustrates examples of tube rack labels 1335A and 1335B in accordance with example embodiments described herein. The tube rack labels 1335 carry consistent label fields and colors such as part name 1410, part diameter 1415, and part image 1425. The tube rack label 1335 may therefor include screw type, screw type abbreviation, screw diameter and color, screw information (as needed), and product picture.

Figure 17:
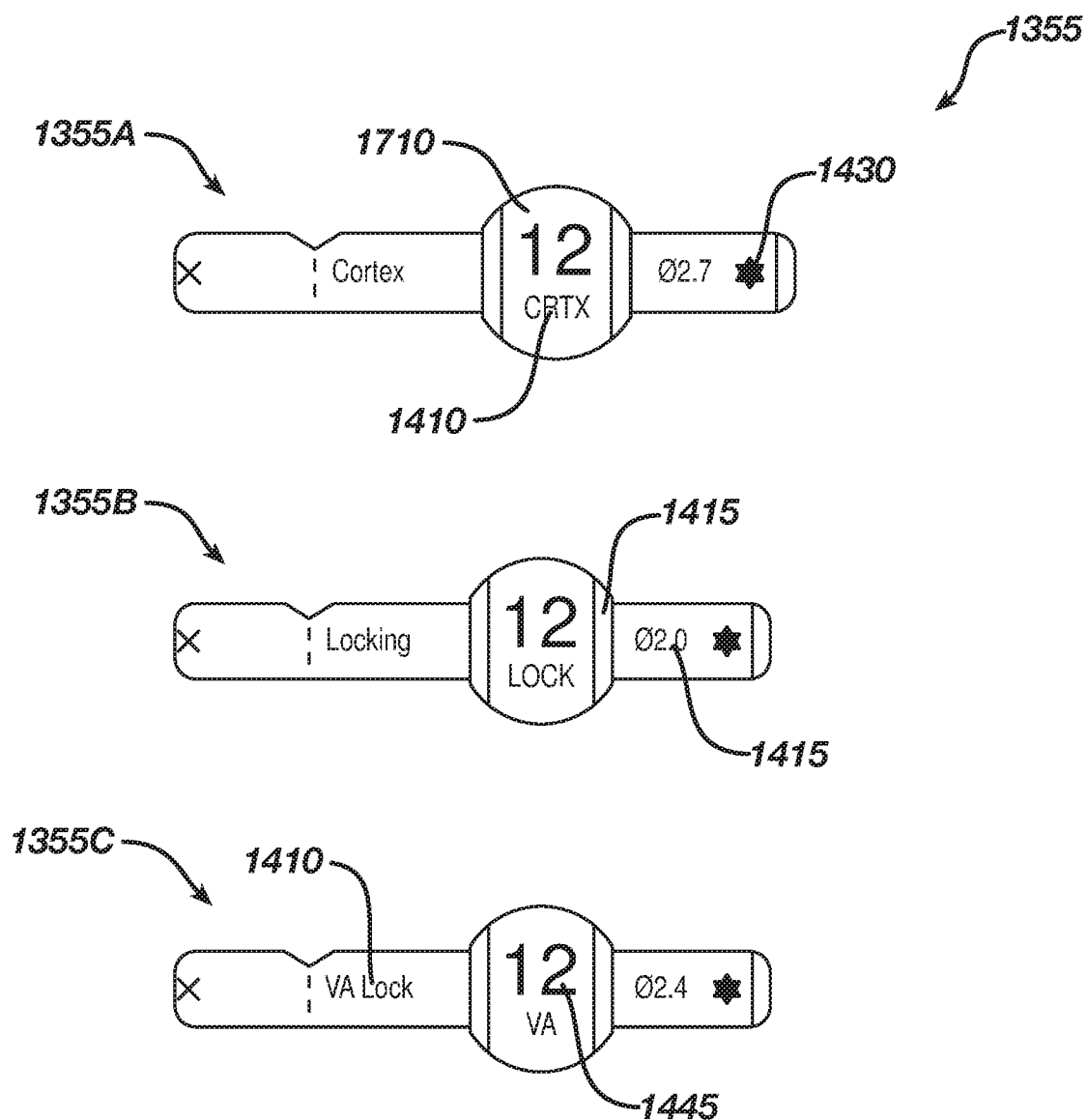
FIG. 17 includes examples of cap labels 1355A, 1355B, and 1355C in accordance with embodiments described herein.

FIG. 17 includes examples of cap labels 1355A, 1355B, and 1355C in accordance with embodiments described herein. As illustrated, the cap labels 1355 have consistent fields such as part name 1410, part diameter 1415, and driver type 1430. The cap label 1355 has been carefully designed such that certain information may be readily obtained by a user from above when looking down into a tube rack apparatus holding a plurality of tubes 1340. In FIG. 17, the large number "12" represents a length 1445 of a screw. The color markings on either side of the length 1445 represent a particular part diameter 1415. The part diameter 1415 is also indicated on a strip that goes along a length of the tube 1340. On other labels such as the cabinet label 1315, drawer label 1325, and tube rack label 1335, the two color and numerical value of diameter are together in one field. In the cap labels 1355, the diameter information is separated. Thus, a single color may represent diameter throughout all of the labels, for easy and quick identification, which may be corroborated by the numerical value. Similarly separated on the cap label 1355 are the naming conventions of the part. On the center portion 1710, an abbreviation of the type of part is written, which is combined with more detailed written information on another side of the cap label 1355. The center portion 1710 may be rounded, rectangular, or other shapes that may convey the desired information. The cap label 1355 may include information such as screw length, screw type, and screw diameter. The regulatory tube label 1345 may include screw diameter, screw diameter color, a second screw identifier, and screw recess (driver type).

Example embodiments also include a method of manufacturing a tube rack apparatus. In accordance with FIG. 1, for example, a method may include forming a bottom portion 110 having a first length L1. A plurality of indents 115 may be formed in the bottom portion 110 and configured to receive tubes and keep tubes straight, the plurality of indents 115 having a lower surface 116 and a higher surface 118, wherein inserted tubes do not pass through the lower surface 116. The method may include forming a plurality of legs 120a and 120b extending from the bottom portion. The method may include forming a top portion 130 having a second length longer than the first length. The method may include joining the top portion 130 to the bottom portion 110. The legs 120a and 120b may be formed continuously with the bottom portion 110. Alternatively, the legs 120a and 120b may be formed continuously with the top portion 130. The method may include forming a plurality of openings 135 in the top portion, the plurality of openings 135 aligned with the plurality of indents 115 of the bottom portion HO. The method of manufacture may also include forming at least one handle member 140 extending from a first end of the top portion 130. The method steps described regarding FIG. 1 may also be used for other example tube rack apparatus example embodiments, of varying size and shape. Once a tub rack apparatus is complete, various label holder may be coupled with the tube rack apparatus to accurately label contents of a tube rack apparatus.

Although the various example embodiments have been described in detail with particular reference to certain exemplary aspects thereof, it should be understood that the invention is capable of other example embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

The invention claimed is:

1. A tube rack apparatus, comprising:
a bottom portion having two ends and a first length;
a plurality of indents formed in the bottom portion and configured to receive tubes and keep the tubes straight and restrict movement of a respective bottom of each of the tubes, the plurality of indents exposing a lower surface of the bottom portion;
at least two legs extending from the ends of the bottom portion;
a top portion having a second length longer than the first length;
a plurality of openings formed in the top portion, the plurality of openings aligned with the plurality of indents;
at least one pair of opposed inwardly curved surfaces which face each other to define an open space,
at least one U-shaped handle member extending upwardly from an end of the top portion; wherein the at least one pair of opposed inwardly curved surfaces are located between the at least one U-shaped handle member and the at least two legs;
wherein the at least two legs extend diagonally upward from the bottom portion to the top portion;
wherein the tube rack apparatus is a first tube rack apparatus;
wherein each open space of the first tube rack apparatus is configured to receive a corresponding U-shaped handle member of a second tube rack apparatus that is identical to the first tube rack apparatus;
wherein each pair of opposed inwardly curved surfaces have lower surfaces which are configured to receive each respective U-shaped handle member of the second tube rack apparatus respectively to stack the first tube rack apparatus on top of the second tube rack apparatus.

2. The tube rack apparatus of claim 1, wherein the at least one U-shaped handle member of the first tube rack apparatus is spaced from the plurality of openings of the first tube rack apparatus by a distance substantially equal to a width of a row of openings from said plurality of openings of the first tube rack apparatus.

3. The tube rack apparatus of claim 1, wherein the top portion of the first tube rack apparatus includes hook members configured to fit into the at least two legs of the bottom portion of the first tube rack apparatus.

4. The tube rack apparatus of claim 1, wherein the at least two legs of the first tube rack apparatus are configured to fit into angled drawers.

5. The tube rack apparatus of claim 1, wherein the top portion, the bottom portion, and the at least one U-shaped handle member of the first tube rack apparatus include rounded corners for ease of user handling.

6. The tube rack apparatus of claim 1, comprising labels configured to be affixed to respective tubes from said tubes.

7. A set of tube rack apparatuses, comprising a first tube rack apparatus and at least one second tube rack apparatus, each second tube rack apparatus being configured to be stacked on the first tube rack apparatus, wherein each tube rack apparatus in the set comprises:
a bottom portion having two ends and a first length;
a plurality of indents formed in the bottom portion and configured to receive tubes and keep the tubes straight and restrict movement of a respective bottom of each of the tubes, the plurality of indents exposing a lower surface of the bottom portion;
at least two legs extending from the ends of the bottom portion;
a top portion having a second length longer than the first length;
a plurality of openings formed in the top portion, the plurality of openings aligned with the plurality of indents;
at least one U-shaped handle member extending upwardly from an end of the top portion; and
at least one pair of opposed inwardly curved surfaces which face each other to define an open space, wherein the at least one pair of opposed inwardly curved surfaces are located between the at least one U-shaped handle member and the at least two legs; and
wherein:
  the at least two legs of each rack extend diagonally upward from the bottom portion of each rack to the top portion of each rack respectively:
  the at least one U-shaped handle member of the first tube rack apparatus is configured to fit within a respective open space defined by a respective pair of opposed inwardly curved surfaces of a respective second tube rack apparatus; and
  the at least one pair of opposed inwardly curved surfaces of the respective second tube rack apparatus has lower surfaces which are configured to receive the at least one U-shaped handle member of the respective second tube rack apparatus to stack the respective second tube rack apparatus on top of the first tube rack apparatus.

\* \* \* \* \*